United States Patent [19]
Ross

[11] Patent Number: 6,023,640
[45] Date of Patent: Feb. 8, 2000

[54] METHOD CONTRIBUTING TO OBVIATING MALE IMPOTENCY

[76] Inventor: Jesse Ross, 321 E. Shore Rd., Great Neck, N.Y. 11023

[21] Appl. No.: 09/280,947

[22] Filed: Mar. 29, 1999

[51] Int. Cl.⁷ .................................................. A61N 1/00
[52] U.S. Cl. .................................. 607/2; 607/39; 600/9; 128/898
[58] Field of Search .......................... 607/2, 39; 600/9, 600/10, 13, 14, 26; 128/898

[56] References Cited

U.S. PATENT DOCUMENTS

| | | | |
|---|---|---|---|
| 3,043,310 | 4/1959 | Milinowski | 607/2 |
| 5,899,922 | 5/1999 | Loos | 607/2 |
| 5,935,054 | 8/1999 | Loos | 600/9 |

*Primary Examiner*—Jeffrey R. Jastrzab
*Attorney, Agent, or Firm*—Myron Amer, PC

[57] ABSTRACT

For impotency due to an inadequate volume of penis-engorging blood, the use of electromagnetic therapy to align the nutrients of the blood in a pearl cell formation in the direction of arterial flow, which contributes, because of lessened flow resistance, to an increased volume of blood adequate for penis-engorgment.

2 Claims, 2 Drawing Sheets

METHOD CONTRIBUTING TO OBVIATING MALE IMPOTENCY

BACKGROUND OF THE INVENTION

The present invention relates generally to improvements for obviating male impotence, the improvements more particularly taking into consideration and being accommodating to the individual main artery system of the penis of the user, all as will be better understood as the description proceeds.

DESCRIPTION OF THE RELATED ART

It is known from medical literature that the delicate balance of blood flow into and out of the penis controlled by "valves" within and muscles surrounding arteries and veins, determines whether a patient is able to achieve an erection of only a short duration, or none at all.

Simply defined in medical parlance, impotence is the failure to achieve erection, ejaculation, or both. Men with sexual dysfunction attribute the condition to a variety of complaints, either singly, or in combination: loss of libido, inability to initiate or maintain an erection, ejaculatory failure, premature ejaculation, or inability to achieve orgasm. Sexual dysfunction can be secondary to systemic disease processes or their treatment, to specific disorders of the urogenital or endocrine systems, or to psychological disturbance. Previously, it was felt that the majority of men with erectly impotency had a psychogenic etiology for their dysfunction since the selection and success of subsequent therapy depends upon the specific etiology it is essential to evaluate all aspects of the erectly mechanism.

For men with vasculogenic impotence this condition is manifested by total erectly impotence, decreased penile rigidity, or loss of erection during intercourse. Vascular insufficiency may be due to aortic occlusion or to more distal atherosclerotic disease in the hypogastric, pudental, and cavernosal arteries. Together with neuropathy, vascular insufficiency contributes to the impotence in many men with diabetes mellitus.

Surgical therapy may be useful in the treatment of decreased potency related to aortic obstruction; however, potency can be lost rather than improved after aortic surgery if the autonomic nerve supply to the penis is damaged. The efficacy of penile revascularization and balloon embolization therapy for vascutogenic impotency remains uncertain. Men with primary venous leak impotency, without associated arterial or sinusoidal disease, may benefit from venous legation. Penile prostheses are the most common therapeutic alternative in impotent patients refractory to other forms of therapy. Even in patients with organic impotence, psychotherapy is often beneficial in alleviating concomitant psychogenic factors that limit the success of medical and surgical therapy.

Focusing on efforts to prevent uncontrolled outgoing or exiting flow, known in medical parlance as venous leakage, prior patents propose devices which squeeze closed the network of veins of the artery system and, in his way, restrict the exiting blood in an attempt to correct the venous leakage. These prior patents are exemplified by U.S. Pat. No. 4,539,980 issued to Chaney for "Male Organ Conditioner" on Sep. 10, 1985 and U.S. Patent Des. 343,246 issued to Gaylor et al. for "Male Erection Sustainer" on Jan. 11, 1994, to mention but a few.

In the operating mode of exiting flow-restricting penis-encircling rings or the like, the extent of pressure applied to squeeze closed the artery system is dictated by size and construction material, and from a specific pressure so dictated by size and construction material. There is little or no deviation or range of pressures. With all known flow-resisting or constricting rings, it frequently occurs that the specific extent of applied pressure is insufficient to obviate venous leakage or, on the other extreme, is excessively high so as to prevent blood engorgement of the penis in the first instance.

BRIEF SUMMARY OF THE INVENTION

As a radical departure from the aforesaid efforts of obviating male impotency by controlling venous leakage, the within inventive method is directed to increasing blood flow to the penis so that it effectively by-passes flow-restricting constraints, and in most instances entirely dispenses with the need of such restraints.

Broadly, it is an object of the present invention to provide a blood flow-enhancing method overcoming the foregoing and other shortcomings of the prior art.

More particularly, it is an object to apply diapulse therapy, well documented in the patent literature, as exemplified by U.S. Pat. No. 3,043,310, heretofore used to accelerate and enhance the healing of wounds, to the problem of obviating male impotency with achievement of solutions equalling that using a drug such as "Viagra" or nitroglycerin, all as will be better understood as the description proceeds.

The description of the invention which follows, together with the accompanying drawings should not be construed as limiting the invention to the example shown and described, because those skilled in the art to which this invention appertains will be able to devise other forms thereof within the ambit of the appended claims.

DETAILED DESCRIPTION

Figure 1:
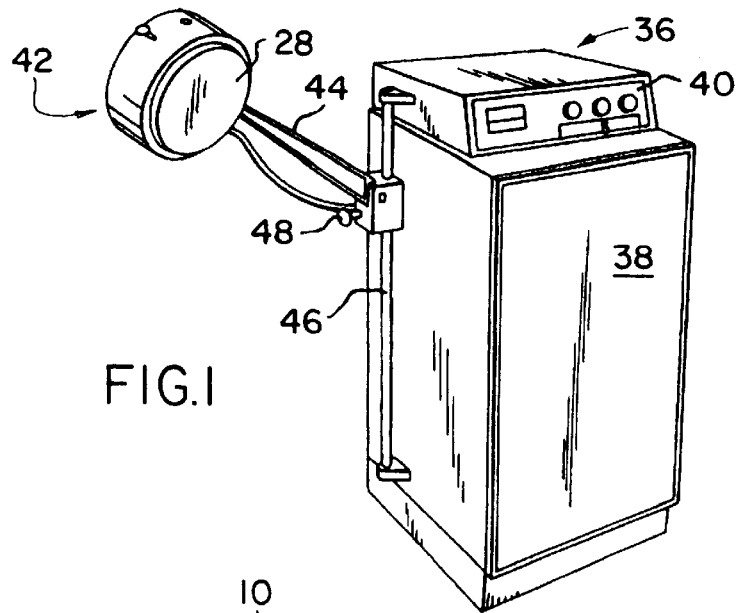
FIG. 1 is a perspective view of an apparatus for generating an electromagnetic field for practicing the within inventive method.

From medical literature it is known that to achieve an erection effective for intercourse, it is necessary to have conditions that allow arterial blood 10 (FIGS. 2 and 3) to build up under high pressure in the erecticle tissue 12 of the corpus cavernosum and corpus spongiosum in the shaft 14 of the penis 16, which pressure buildup will occur since the voids of the erectile tissue 12 or, more particularly the venos sinusoids and endothelial cells 18 thereof, are initially empty and outflow therefrom partially occluded. The transformation from empty to full with a partially occluded outflow effectively maintains the high pressure within the sinusoids 18 causing ballooning of the erectile tissue 12 to such an extent that the penis 16 becomes hard and elongated.

Figure 6:
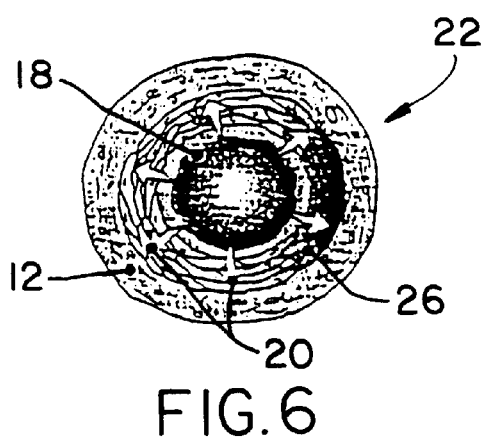
FIGS. 6 and 7 are cross sectional views, in enlarged scale, of anatomical features at locations circumscribed by arrows 6—6 and 7—7 respectively, on FIG. 5.
Figure 7:
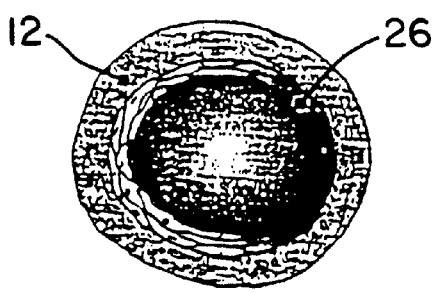

To the same end as the above, it is known that nitric acid 20 effect the blood vessels 22 (FIGS. 6 and 7) of the erectile tissue 12 by causing the dilation thereof and in this manner contributes to blood flow 24 into and engorgement of the penis. This is explained in the medical literature that endothelial cells, i.e., surface cells inside the blood vessel, as at 26, release the gas nitric oxide 20 either naturally or when prompted by a drug such as "Viagra" or nitroglycerin. The gas nitric acid penetrates the smooth muscle cells and relaxes them, allowing the blood vessel 22 to dilate.

At this point it is important to note that the within inventive method contributes to the release of the gas nitric acid 20 naturally by delivering blood and its nutrient contents (FIGS. 3, 4) to the endothelial cells 18, a delivery which does not occur for an impotent male or, if it does, is insufficient in volume to result in a meaningful release of the gas nitric acid.

Underlying the present invention is the recognition that the use of known so-called diapulse therapy can contribute to the natural release of the gas nitric acid 20 and also restore a lacking of sensitivity of nerves, a condition known in medical parlance as neuropathy, due to lack of blood flow and activity in the penis, of an impotent male.

For a better understanding of the medical explanation which follows of the within inventive method, it is helpful to consider one generally well known and understood principle of fluid dynamics and another circumstance known by common experience. The principle of fluid dynamics is that if bunker C oil, which has a heavy viscosity, is poured through a two-inch pipe, it will move at a fixed speed. However, when #2 oil, which has a lesser viscosity, is substituted, it will flow through the same pipe at a much greater speed.

The circumstance known by common experience is that comparing a six-lane highway where the vehicles change lanes at will, thereby reducing the speed of traffic, with traffic which remains in specific lanes, the latter will move much more rapidly.

As will be explained in greater detail as the description proceeds, an effective use of diapulse therapy using the "Treatment Head For Atherapeutic Apparatus" of U.S. Pat. No. 3,043,310, has confirmed in several performed experiments that to relieve smooth muscle spasm, method parameters most effective are using 80, 160 or 300 pulses per second, with a pulse width of 65 micro seconds, and using a power setting for 4 inch, 5 inch, or 6 inch penetration.

Exposure of injured nerves to diapulse therapy at higher pulses per second accelerates nerve regeneration, thus effectively restoring sensitivity of the nerves in overcoming neuropathy, as well as regenerating nerves that have been in any way damages.

The application of diapulse therapy consists of exposing the groin and penis of the impotent male to the electromagnetic filed of head 28.

Figure 2:
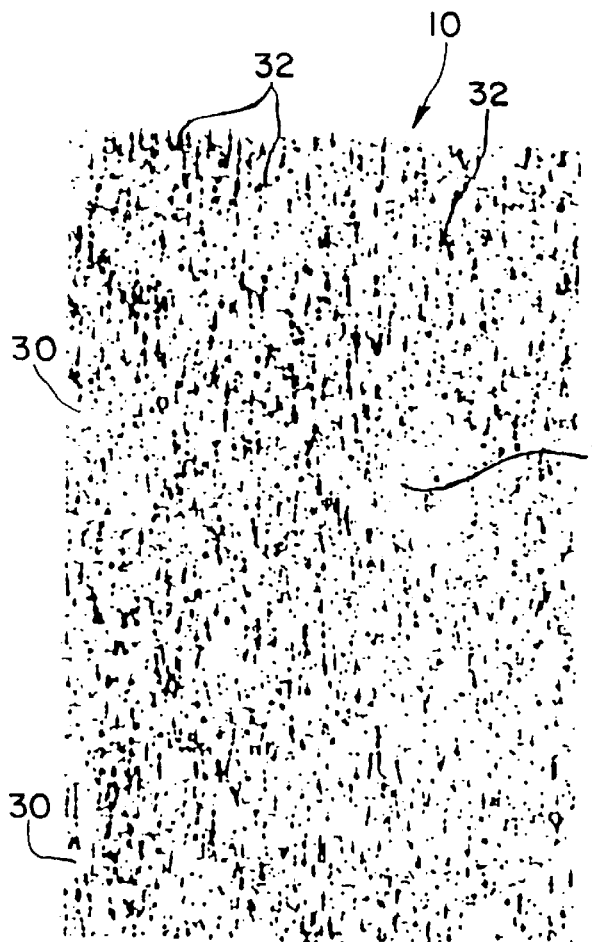
FIG. 2 is an illustration of a microphotograph of blood prior to the subjection to high frequency oscillation.
Figure 3:
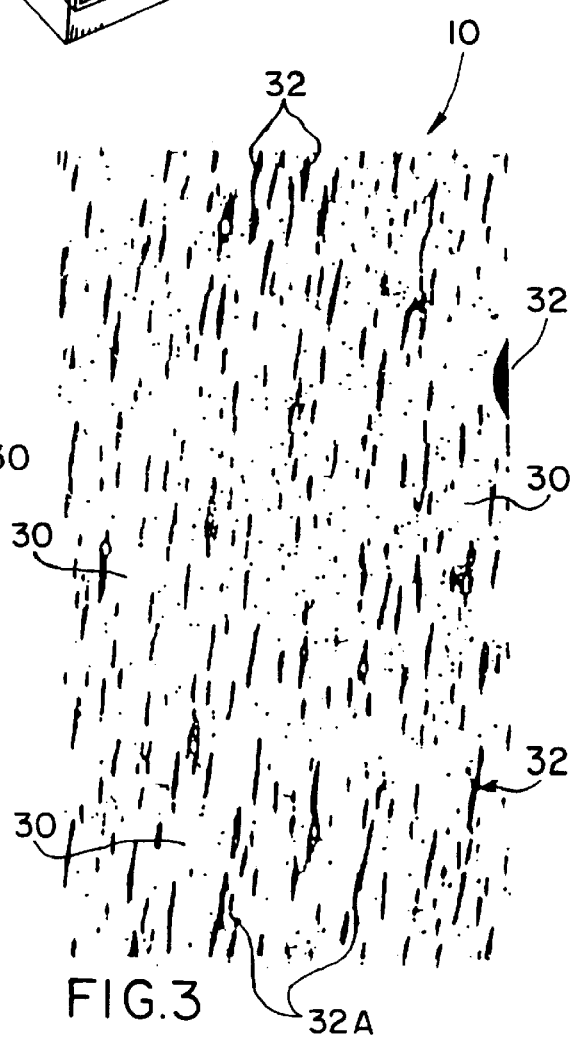
FIG. 3 is another microphotograph illustration of the blood of FIG. 2, but after subjection to the high frequency oscillation and showing a pearl chain formation of the nutritive blood elements.
Figure 4:
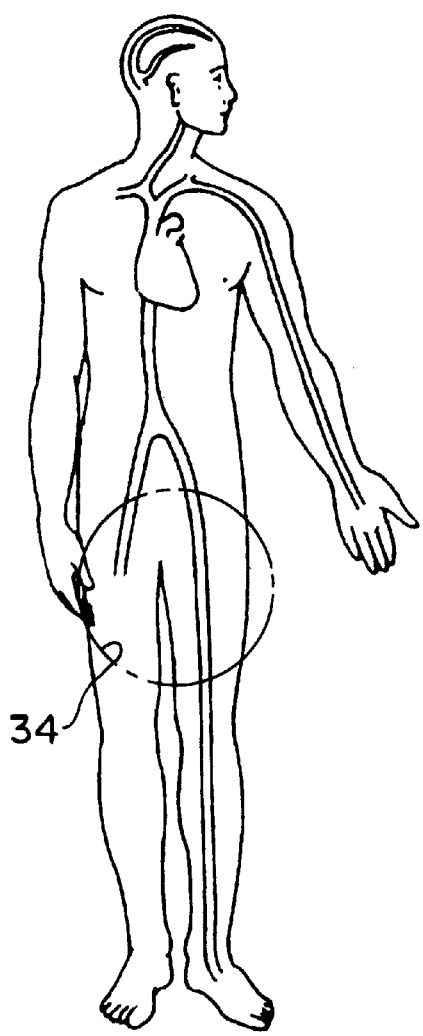
FIG. 4 is a graphic of blood circulation.

The result of the impingement or exposure of the electromagnetic field on the blood is best understood from FIGS. 2 and 3, to which reference should now be made. Blank or unoccupied areas, individually and collectively designated 30 will be understood to be the fluid content of the blood, and the occupied areas, also individually and collectively designated 32, will be understood to be the nutritive elements of which the blood is composed, such as lymph, chyle, plasma, etc.

By comparison of FIG. 2, before subjection to the electromagnetic field, to FIG. 3 after subjection, it should be readily observable that the pattern of FIG. 2 is a random dispersion of the blood fluid and nutritive elements contents 30, 32, and that in FIG. 3 the nutritive elements 32 have assumed a chain-like formation, more particularly designed 32A, which formulation is known in the parlance of the art as a "pearl chain" formation.

Figure 5:
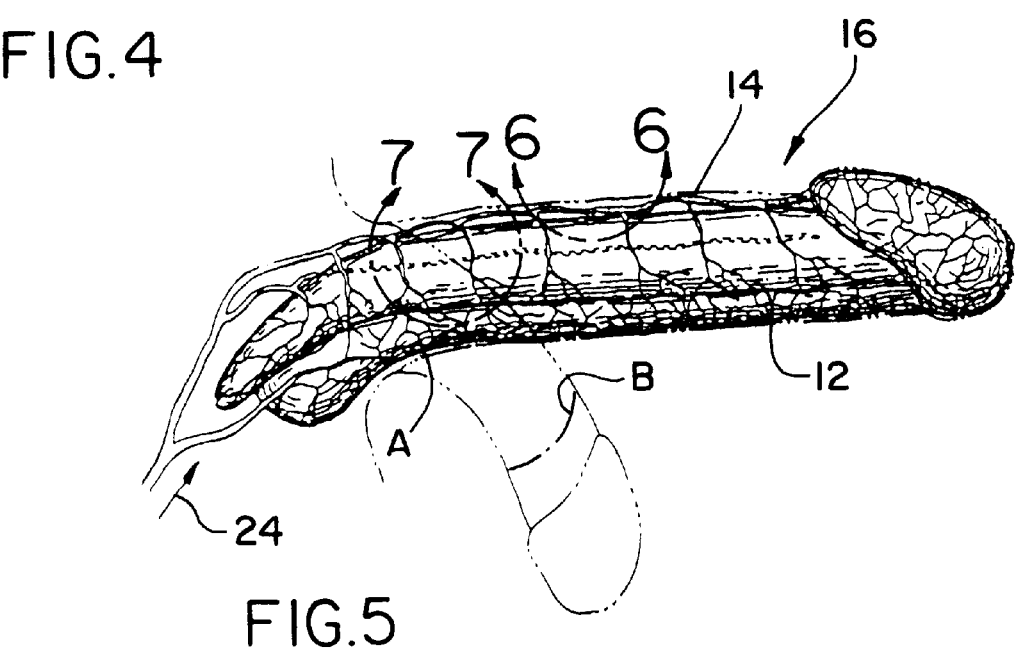
FIG. 5 is a side elevational view of a penis in a flaccid condition as illustrated in a triple dot reference perspective, and in full line in its erectile condition illustrating the main artery system thereof.

As best understood from FIG. 5, the nominal penetration of the extent of blood flow without diapulse therapy is at location A, and the significantly increased penetration is at location B, due to the flowability of the blood resulting from the pearl chain formation of the blood.

The dispulse therapy, which creates an alignment of blood cells or the noted pearl chain formations of FIG. 3, has been found in practice to increase the velocity of blood through the vessels by 1.75 times a testing pulse of "100". To this end, to measure blood flow to the groin and penis area 34 which is the site of therapy, use may be made of the Doppler system, well known in medical literature, as well as of pneumoplethysmography, and the use of a volumetric pleythsmograph.

For completeness sake, it is noted that in FIG. 1 there is the previously noted referred to "Treatment Head For Atherapeutic Apparatus" of the '310 patent, used for what is referred to herein as "diapulse" therapy. More particularly, shown in FIG. 1 is an athermapeutic apparatus for the generation of pulsed high frequency oscillations to which a patient is subjected of a type which is now well known to the art wherein the pulse frequency and duration is of such nature that the total time period during which electrical energy is actually induced into the body of a patient is so short that despite the comparatively high instantaneous energy level of the pulsed power it is unaccompanied by heat generation because the time for heat dissipation is many times longer than the heat accumulation. The athermapeutic apparatus 36 as therein shown comprises a cabinet 38 provided with a control panel 40, for regulating the pulse repetition rate and pulse duration, timer setting, etc., and having a treatment head 42. Such treatment head is carried by an arm 44 to which it is pivotally connected, and with the arm in turn being reciprocally and axially movable on a tubular support 46 and secured in any desired adjusted position relative to the support 46 by a locking screw 48.

Apparatus 36 will be understood to generate an electromagnetic field having a pulse duration and frequency which is fixed at sixty five-micro-seconds and for pulse frequencies of from eighty to six hundred pulses per second, so that even at its maximum setting the total peak energy of nine hundred seventy five watts maximum is of such short duration that the average power is only thirty eight watts at maximum setting. Accordingly, at the maximum pulse rate of six hundred pulses per second the rest period between the pulses is approximately twenty-five times as great as the duration of each pulse, so that any heat that might be accumulated in the patient during the occurrence of the pulse has many times longer for its dissipation, thereby providing a treatment eliminating any heating effect that could be harmful to the patient.

In diapulse therapy using the apparatus 36, the electromagnetic field utilized might typically have the following specific parameters:

1. A frequency of 27.12 megahertz (11 meter band);
2. A pulse repetition rate of 80 to 600 pulses per second;
3. A pulse width of 65 microseconds;
4. A power range, per pulse, of between 293 and 975 watts;

5. A duty cycle between ½ of 1% to 3.9%; and

6. A square pulse, with a rise and fall time less than 1%.

Studies to date indicate that good results in obviating male impotency with diapulse therapy are achieved with the noted exposure, for ten to thirty minutes, three times a week for six weeks, at settings of 400 pulses per second. The selection of the depth of penetration of 4, 5 or 6 inches is dependent upon the obesity of the patient bone density and tissue condition which, in severe cases, might warrant using 400 pulses per second in exposure intervals increased to ten to thirty minutes each, three times a week, for an additional six weeks. It is to be noted that there is no limitation of exposure during diapulse therapy on a daily basis or even twice per day since there are no contradictions to the use of this therapy. Specifically, in cases of neuropathy, the extracellular calcium measurements in both the spinal cord and peripheral nerve, excessive amounts of calcium is accumulated which prevents regeneration of nerve or spinal cord. The application of diapulse therapy at settings of 500 or 600 pulses with 4, 5, or 6 power settings, significantly alters calcium distribution.

For impotency from smooth muscle spasm, good results were achieved, as previously noted, using pulsations of 80, 160 or 300 pulses.

While the apparatus for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A method contributing to obviating male impotency comprising the steps of exposing a male's groin and penis area to generated eletromagnetic radiation of selected parameters, selecting as said parameters one of either 400, 500, or 600 pulses per second with a pulse width of 65 microseconds, maintaining said exposure at said parameters monitoring blood flow until the velocity thereof is at least 1.75 times a selected testing pulse of said male, and repeating said exposure to said generated electromagnetic radiation at intervals of selected duration until the treated male's penis naturally can assume an erectile condition, whereby there is a release of the gas nitric acid and an obviating of neuropathy during said repeated exposures to contribute to successive naturally assumed erectile penile conditions to enable the dispensing of the repetitions of said exposures.

2. The method as claimed in claim 1 using pulsations of 80, 160 or 300 pulses to obviate impotency from smooth muscle spasm.

* * * * *